United States Patent [19]

Warriner

[11] Patent Number: Plant 5,318

[45] Date of Patent: Nov. 6, 1984

[54] ROSE PLANT JACNON 74-183

[75] Inventor: William A. Warriner, Tustin, Calif.

[73] Assignee: Jackson & Perkins Company, Medford, Oreg.

[21] Appl. No.: 404,045

[22] Filed: Aug. 2, 1982

[51] Int. Cl.[3] ..... A01H 5/00

[52] U.S. Cl. ..... Plt./20

[58] Field of Search ..... Plt./18–20

*Primary Examiner*—James R. Feyrer

*Attorney, Agent, or Firm*—Klarquist, Sparkman, Campbell, Leigh & Whinston

[57] ABSTRACT

A new variety of floriferous rose plant which is vigorous, well branched with orangey red flowers having stiff petals of firm substance.

1 Drawing Figure

This present invention relates to a new and distinct variety of rose plant of the hybrid tea class which was originated by me by crossing the variety Baccara, U.S. Plant Pat. No. 1,367, expired, with an unnamed variety.

The primary objective of this breeding was to produce a new rose variety combining the substance and color of Baccara with plant habit and floriferousness of the pollen parent. This objective was substantially achieved along with other desirable improvements as evidenced by the following unique combination of characteristics which are outstanding in the new variety and which distinguish it from its parents, as well as from all other varieties of which I am aware:

1. An orangey red flower, R.H.S. group 39.
2. Stiff petals of firm substance.
3. Vigorous, well branched, floriferous plant.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Baccara, U.S. Plant Pat. No. 1,367.

*Pollen parent.*—Unnamed variety.

Classification:

*Botanical.*—Rosa hybrid.

*Commercial.*—Hybrid tea.

FLOWER

Observations made from specimens grown in Wasco, Calif. in July.

Blooming habit: Continuous.

Bud:

*Size.*—One inch when petals start to unfurl.

*Form.*—Short, pointed ovoid.

*Color.*—When sepals first divide, red group 47B and 47D. When half blown; upper side of petals red group 47A, lower side of petals red group 47C.

*Sepals.*—Color: Outer surface green 138A. Three appendaged sepals normally appendaged. Two unappendaged sepals hairy edged.

*Receptacle.*—Color: green 137A. Shape: funnel. Size: large, broad. Surface: smooth.

*Peduncle.*—Length: medium. Surface: nearly smooth. Color: bronzy. Strength: stiff, erect.

*Opening.*—Petals fold outward with very little petal curling.

Bloom:

*Size.*—Large. Average open size 4–4½ inches.

*Borne.*—Singly.

*Stems.*—Long, strong.

*Form.*—When first open: flat. Permanence: retains its form to the end.

*Petalage.*—Number of petals under normal conditions, 40 to 50.

*Color.*—Center of flower: Upper side of petals, red group 39A. Reverse side of petals, red group 39A. Base of petals, small area at point of attachment, pale yellow (dictionary definition). General tonality from a distance, red group 39A.

*Variegations.*—Occasional darker streaks in outer petals.

*Discoloration.*—Only slight fading.

*Fragrance.*—Slight.

Petals:

*Texture.*—Thick, stiff.

*Shape.*—Round.

*Form.*—Flat.

*Arrangement.*—Imbricated. Petaloids in center, few and small.

*Persistence.*—Drop off cleanly.

*Lastingness.*—On the plant: long. As cut flower: long.

Reproductive parts:

*Anthers.*—Medium. Color: yellow. Arrangement: regular around styles.

*Filaments.*—Color: reddish.

*Pollen.*—Lemon yellow.

*Styles.*—Color: reddish.

*Stigmas.*—Color: white.

PLANT

Form: Bush.

Growth: Vigorous, upright, branching.

Foliage:

*Size.*—Medium.
*Quantity.*—Normal.
*Color.*—New foliage: red purple 59A. Old foliage: Green 136A.

Leaflets:
*Shape.*—Ovate to obovate.
*Texture.*—Upper side: leathery.
*Edge.*—Serrated.
*Serration.*—Single, small.
*Petiole.*—Rachis: Color: green. Upper edge has numerous small prickles. Underside: prickles.
*Stipules.*—Long, bearded.
*Disease resistance.*—Resistant to mildew under normal growing conditions at Irvine, Calif.

Wood:
*New wood.*—Color: dark green. Bark: smooth.
*Old wood.*—Color: green with reddish overlay. Bark: smooth.

Prickles:
*Quantity.*—On main stalks from base: ordinary. On laterals from stalk: ordinary.
*Form.*—Very long base, medium, hooked downward.
*Color when young.*—Brown.
*Position.*—Irregular.

Small prickles:
*Quantity.*—On main stalks: few. On laterals: few.
*Color.*—Brown.

I claim:

1. A new and distinct variety of rose plant of the hybrid tea class, substantially as herein shown and described, characterized particularly as to novelty by the unique combination of its orange-red, heavily substanced flowers borne on its vigorous, heavily branched plant.

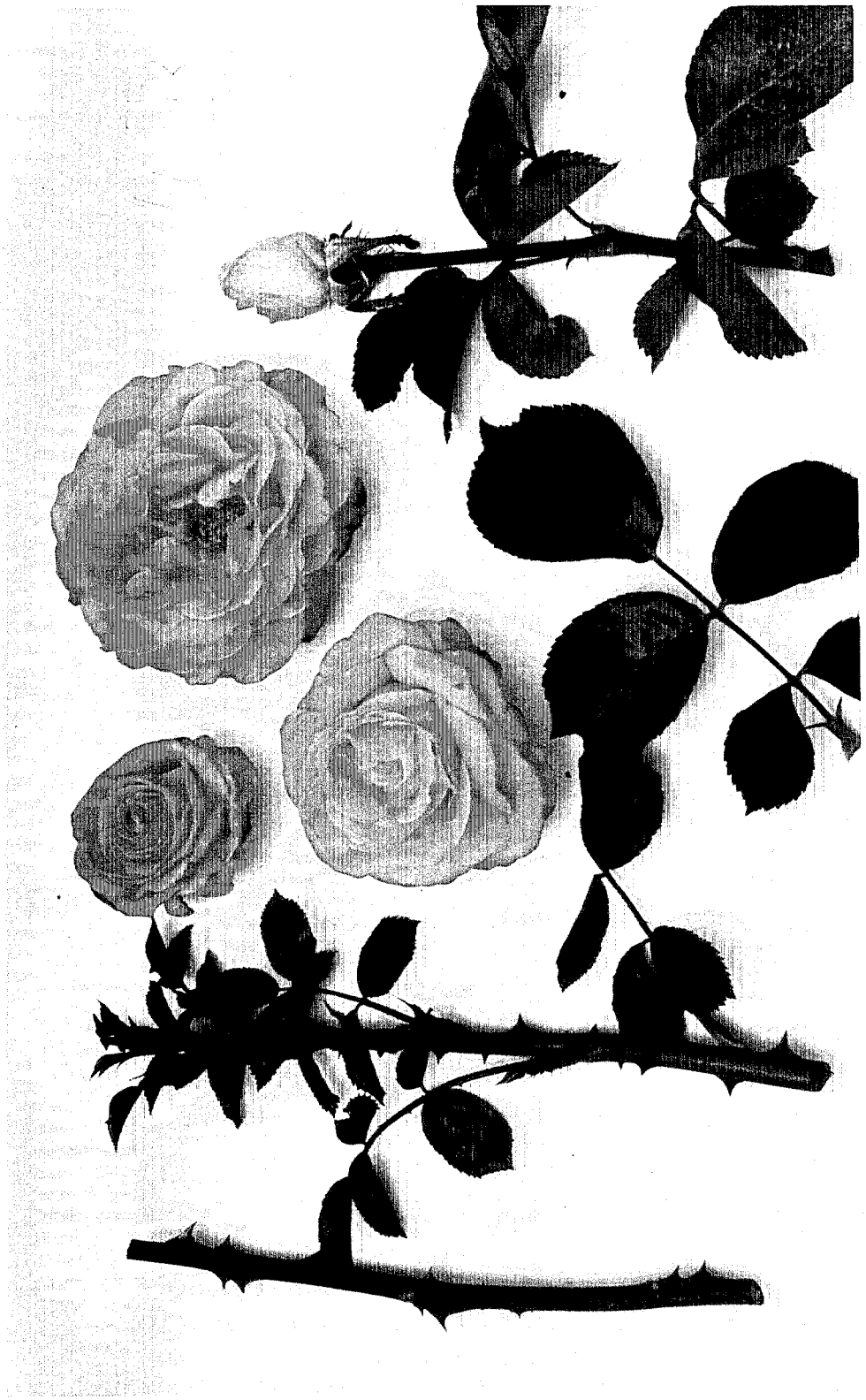

* * * * *